United States Patent
Detrick

(10) Patent No.: US 6,180,565 B1
(45) Date of Patent: *Jan. 30, 2001

(54) MICRO-SIZED WEED AND FEED PARTICLES HAVING ENHANCED PROPERTIES

(75) Inventor: John H. Detrick, Birmingham, AL (US)

(73) Assignee: Pursell Industries, Inc., Sylacauga, AL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/720,752

(22) Filed: Oct. 1, 1996

(51) Int. Cl.$^7$ ............................. A01N 25/12; A01N 25/26
(52) U.S. Cl. ........................... 504/145; 504/323; 504/367
(58) Field of Search ..................... 504/145, 323, 504/367

(56) References Cited

U.S. PATENT DOCUMENTS 3,778,248 * 12/1973 Weston et al. .................. 71/115
4,711,659 * 12/1987 Moore ............................. 71/93
4,971,796 * 11/1990 Sjogren ........................... 424/417

OTHER PUBLICATIONS

Ross et al. *Applied Weed Science*. Burgess Pub. Co.: Minneapolis. p. 107–110. 1985.*

* cited by examiner

*Primary Examiner*—S. Mark Clardy
(74) *Attorney, Agent, or Firm*—Breiner & Breiner

(57) ABSTRACT

Herbicide-fertilizer combination granular products are described comprising singular, or blended, basic fertilizer granular materials and impregnated with or coated thereon a herbicidal material for controlling broadleaf weeds postemergence. The weed and feed fertilizer products uniquely are characterized by the size, weight and physical property of the fertilizers and any filler particles contained in the weed and feed fertilizer blend product in that the particle size is substantially in the micro-sized range of 500 to 1500 microns; the particle weight generally is less than one-tenth that of customary regular-sized weed and feed particles; and there is a greater cohesion of the particle to the weed foliage. These micro-sized particles exhibit a significantly higher incidence of contact with and greater adhesion to the foliage of weeds thus providing superior weed control.

8 Claims, No Drawings

MICRO-SIZED WEED AND FEED PARTICLES HAVING ENHANCED PROPERTIES

FIELD OF INVENTION

The present invention relates to improved granular fertilizer plus herbicide formulations (weed and feed) used to control weeds in and provide nutrition to turfgrass. More particularly, the present invention relates to weed and feed formulations wherein superior postemergence weed control is obtained utilizing micro-sized particles (1.0 mm) of a fertilizer material, and preferably a blend of various fertilizer materials, as the carrier for the herbicide(s). The weed control obtained is significantly superior to that obtained from the customary regular-sized (2.5 mm) weed and feed products made from blended fertilizer materials.

BACKGROUND OF INVENTION

Herbicides used on turfgrasses generally fall into two categories:

1. Preemergence herbicides, which must be applied prior to the germination of monocotyledon annual weed grass seeds, such as crabgrass, annual bluegrass (poa annua), etc., most commonly are mytotic root inhibitors. These inhibitors prevent emergence and growth of the weed grass shoot by preventing the root from developing as it emerges from the seed. These herbicides are active in the soil where their presence in the soil or at the soil surface prior to seed germination is essential for efficacious herbicidal performance. Accordingly, these herbicides commonly are applied as a granular product, such as small 1.0–1.5 mm clay granules or 2.0 mm–2.5 mm fertilizer granules which have 1% to 2% of the herbicide active ingredient absorbed or coated onto the granule surfaces. These granules, when distributed, penetrate through the turfgrass foliage to the soil surface where the herbicide desorbs from the granule into the soil solution. Preemergence herbicides commonly used are in a family of dinitroaniline chemicals, such as benefin, trifluralin, and oryzalin. This category of products are generally described in U.S. Pat. Nos. 3,705,794; 3,798,276; 4,063,929 and 4,025,329 which describe products having varying particle sizes.

2. Postemergence herbicides are applied to weed foliage after emergence from dicotyledon seeds, commonly referred to as broadleaf weeds, such as dandelion, plantain, white clover, henbit, spurge, etc. These are systemic auxinic herbicides which require foliar absorption and subsequent translocation within the weed plant for efficacious weed kill. These herbicides commonly are mixed in water or liquid fertilizers and applied as liquid sprays. Liquid droplet size in the spray is controlled by pressure and orifice size. Droplet sizes of about 500 to 2000 microns generally are acceptable. Air currents present during application can cause undesired drift of droplets, which-are too small (less than 200 microns), onto foliage and kill susceptible, desired plants such as ornamental and vegetable plants. Liquid-sprayed postemergence auxinic herbicides commonly used in turfgrass applications are phenoxy and benzoic chemicals, such as 2,4-dichlorophenoxy-acetic acid (2,4-D), 4-chloro-2-methylphenoxy acetic acid (MCPA), 2-(4-chloro-2-methyl phenoxy) propanoic acid (mecoprop), and 3,6-dichloro-2-methylbenzoic acid (dicamba).

Combination postemergence herbicide-blended granular fertilizer products, often referred to as "Weed and Feed" (W&F) products, were developed for weed control and fertilization in residential lawns. They are used by the do-it-yourself homeowner and lawn service companies to save time and money with the dual value product—herbicide plus fertilizer—in one application. Blended turfgrass fertilizers, customarily comprised of regular-sized granular basic fertilizer materials, nominal size, 2.5 mm, are sourced from among such regular-sized materials as urea, coated urea, ammonium sulfate, ammoniated phosphate, potassium chloride or sulfate, and non-nutrient filler granules such as sized limestone granules. These regular-sized blended fertilizers were reformulated as W&F products by replacing the heavy fillers with lightweight particles of the same compatible regular size, such as ground corn cob and granulated peanut shells. These light particles then are referred to as lightweight carriers for the herbicides. This entire blend of regular-sized heavy granular fertilizer materials and lightweight granular carriers is impregnated or coated with the postemergence herbicides by the W&F manufacturer.

When the W&F is spread by the homeowner onto the weedy lawn turfgrass, it is a labeled direction for use to either water the turfgrass first or apply the W&F when the turfgrass is wet with dew. This is required to provide the adhesion of the fertilizer and carrier particles to any prostrate or upright weed foliage with which they come into contact during the spreading application. However, despite the moistened weed foliage, most of the regular size, heavy fertilizer granules, rather than adhere to, rebound from the weed foliage to the soil below. While some of the lightweight carrier particles in the blend do adhere effectively to the weed foliage, their presence in the W&F product generally is less than 30% of the total granules so there is low contact frequency with the population of weed foliage present in the turfgrass area to which the regular-sized W&F is applied.

Further, at the nominal 2.5 mm size of regular blended fertilizers/carriers used in residential W&F products, which generally are in a distribution of granule particle sizes from 1.5 mm to 3.0 mm (1500 to 3000 microns), the number of regular-sized particles spread or distributed onto the turfgrass typically is in the range of 150 to 300 total particles per square foot. However, only about 10% to 25% of the total number of those particles are the lightweight carrier particles. Consequently, the distribution of particles, which reasonably might contact and adhere to the weed foliage, is only in the range of 15 to 75 particles per square foot, or about from one carrier particle per 10 square inches to one carrier particle per 2 square inches of turfgrass area.

Consequently, the weed control afforded by these regular-sized granular blended fertilizers and lightweight carriers impregnated with postemergence herbicides repeatedly has been significantly inferior to that of liquid spray-applied postemergence herbicides. In these granule vs. liquid herbicide comparisons identical herbicides are compared at the same applied rates, usually expressed as weight of herbicide active ingredient per unit area, such as per acre. The liquid herbicide-treated area for the comparison is separately prefertilized with a granular fertilizer at the same nutrient treatment rate as that of the regular-sized granular W&F treatment.

Generally, weed control ratings of these two applications, depending on the applied herbicide rate, at four to five weeks after treatment are:

|   | Treatment | % Weed Control | |
|---|---|---|---|
|   |   | Range | Typical |
| 1. | Liquid spray herbicide and separately applied granular fertilization. | 85–100 | 90 |
| 2. | Weed and Feed granular, blended herbicide-fertilizer combination product. | | |
|   | Regular size (2.5 mm) | 10–60 | 30 |

Accordingly, there is a need for a granular weed & feed product which has weed control approaching the weed control of a liquid spray herbicide. The present invention relating to postemergence herbicides applied as weed & feed granules, meets that need.

SUMMARY OF INVENTION

A solution to the problem of poor weed control by conventional regular-sized, granular, postemergence herbicide-blended fertilizer combination Weed and Feed products was discovered by the present inventor when identical formulations were prepared using basic fertilizer materials and carriers but with reduced particle size (micro size). The micro sized particles are comparable to the low end of the size range of the droplets of liquid spray-applied postemergence herbicides. This particle size reduction from the regular size, 1.5 mm to 3.0 mm (2.5 mm nominal) range down to a micro size, 0.5 mm to 1.5 mm (1.0 mm nominal), or 500 microns to 1500 microns (1000 microns nominal), range accomplishes the following:

1. Particle count and distribution per unit area of the micro size particles will be more than 15 times the particle count and distribution of the regular-sized W&F product. More particles applied mean more weed foliage "targets" are contacted. In addition, the entire number of micro sized particles, both fertilizer and carrier particles, are lightweight in the micro size. When only the number of lightweight particles in the regular-sized blend are compared with the entire micro-size particles the disparity between the number of regular- and micro-sized weed foliage adhering particles is even more apparent.

| W&F Particle Size | Distribution-particles per ft² | |
|---|---|---|
|   | Entire Blend | Lt. Wts. Only |
| Regular (2.5 mm) | 150–300 | 15–75 |
| Micro (1.0 mm) | 3000–4500 | 3000–4500 |

2. Micro-size particle weights generally are less than 10% of those in the customary regular-sized W&F blended products. For example, a 1.0 mm urea particle contained in the micro blend would weigh only about 6% of the weight of the 2.5 mm urea granule in the regular blend and about 9% the weight of the regular-sized peanut shell granule carrier. These lighter micro-sized particles will have less rebound energy from the weed foliage with which they come into contact. Further, when applied to wetted foliage, as is recommended by the directions for use, the inclusion of a high percentage of hygroscopic and highly soluble microsized urea particles in the blend additionally assures adhesion of these urea particles, which are coated with the selective postemergence herbicides, to the moistened weed foliage. When adhered these particles undergo rapid moisture absorption and quickly begin particle surface dissolution, which facilitates translocation of the herbicides to and into the weed leaf tissue. Micro-sized urea prill is produced principally as a nitrogen-protein supplement for use in cattle feed, so the present use of micro-sized urea prill as a postemergence herbicide carrier is a unique use.

Identical W&F formulations in the two sizes—regular (2.5 mm nominal) and micro (1.0 mm nominal)—applied to prewatered weed foliage are compared in performance with liquid spray-applied herbicides at 4 to 5 weeks after treatment:

|   | Treatment* | % Weed Control | |
|---|---|---|---|
|   |   | Range | Typical |
| 1. | Liquid spray herbicide and separately applied granular fertilization. | 85–100 | 90 |
| 2. | Weed and Feed granular, blended herbicide-fertilizer combination product. | | |
|   | a. Regular size (2.5 mm) | 10–60 | 30 |
|   | b. Micro size (1.0 mm) | 50–100 | 75 |

*Herbicide and nutrient rates of application per unit area are equal among all treatments.

As can be seen, the micro-sized W&F weed control typically is more than twice that of the regular-sized W&F. Importantly, the micro-sized W&F weed control approaches the weed control of the liquid spray-applied herbicide but without need for the additional step of fertilizer application.

The micro particle size both lowers the weight of each particle, and increases the numbers of particles distributed per unit urea, which increases contacts with weed foliage. The inherent hygroscopicity, high water solubility and dissolution rate of the micro-sized urea particles increase particle adhesion to weed foliage which they contact and enhance translocation to and within the weedleaf tissue of the systemic auxinic herbicides present on the urea granule surface.

PREFERRED EMBODIMENTS OF INVENTION AND COMPARATIVE TESTS

In the presently described and other studies and with all products tested, in accordance with the present invention, fertilizer particles of the weed & feed products, whether they be urea, coated urea, ammoniated phosphate, potassium sulfate or a combination of these as blended fertilizers, are impregnated or coated with the postemergence herbicides in the selected range. Additionally, when inert lightweight fillers, such as granulated peanut shells and the like, are utilized as carriers, these carriers are impregnated or coated with the herbicide in the designated amount. Typically, the herbicide, depending upon the herbicide selected, will be applied to the fertilizer particles at a concentration of approximately 0.5 to 10% by weight of the total fertilizer and inert carrier weight. The application can be made by impregnation or other coating process from a liquid solution of the herbicide, or by bonding a powder form of the herbicide with a liquid sticking agent, or by utilizing other known conventional methods of impregnation or coating. If the weed & feed products are to contain a blend of basic fertilizer materials, the blending is carried out using conventional blending processes and techniques well known in the art.

Field research was conducted to evaluate the effect of four different micro-sized particle components, which are used in the micro-sized Weed & Feed blend according to the present invention. Each particle component was used singularly as the herbicides carrier treatment. Three herbicides as powders: 2,4-D, MCPP and Banvel® (dicamba), a powder premix under the acronym trade name DMB, were bonded with glycol/water on each carrier. Each micro-sized particle treatment was applied at the same particle count per unit area and at the same herbicides rate per unit area. Also included as a carrier in these studies was a well recognized commercial turf builder fertilizer, which is a homogeneous NPK particle, not a blend, that customarily is supplied in a much wider particle size range. However, for these tests larger oversize and smaller undersize particles were removed by screening, such that the homogeneous NPK particles retained for the tests were of the same particle size range as the four micro-sized fertilizer particle treatments falling within the scope of the present invention.

Further, a regular-sized urea particle, which nominally is 2.5 mm compared with the 1.0 mm micro-sized particle, also was used as a comparative control. The regular-sized urea treatment with herbicides was applied at the same product weight and herbicide rate as the micro-sized urea treatment. Consequently, the regular-sized urea was applied at a significantly lower particle count per unit area than the micro-sized urea. The herbicides rate in all six application treatments was the same.

In the present study, the six carriers utilized were micro size urea, micro size polymer coated urea, regular size urea, micro size sulfate of potash granules, micro size granular peanut hull, and a commercial turf builder fertilizer carrier, which was screened to the same size range as the micro size urea and the other micro size carrier particles, i.e., all larger particles and all small particles of the commercial product were removed by screening and is designated herein as micro CFC. The objectives of the study were: 1) to directly compare the value of each of the various micro size carriers when applied at the same herbicide rate and particle distribution per unit area to make their weed control effect independent of particle coverage, and 2) to directly compare the value of the micro size particle treatments with the regular size treatment. The resulting differences in performance values among the micro size carriers would be inherent in their particle density or other chemical or physical properties of the various particles, such as hydroscopicity, adsorptivity and dissolution rate. Excepting regular size urea, treatments of the five micro size carriers were of the same particle size but varying particle density and bulk density. They were so formulated with the DMB herbicides to deliver 2.0 acid equivalent (ae) per acre when the applied particle count per unit area of each was a constant at about 3400 particles/sq.ft. As a control comparison of regular size weed & feed formulations, regular size urea carrier with the same DMB herbicides was applied at 200 lb product/acre, equal in weight and approximate volume to the micro size urea carrier in the test, but lower in particle distribution by an order of magnitude, about 240 particles/sq.ft. because of its larger particle size. Accordingly, weight and volume of the materials applied and the herbicide concentration on carriers varied by treatment as shown in Table 1 hereinafter.

The study was conducted by university researchers on the grounds of Mississippi State University. Five replications of six treatments were established. Treatment was preceded by irrigation using a tractor sprayer. Measurement plots were 3'×3' nested within a 4'×4' plot grid. The area was over seeded in the fall of 1995 with white clover (*Trifolium repens*) and buckhorn plantain (*Plantago Ianceolata*). Treatments as applied were unbalanced nutritionally so that supplemental fertilizers were formulated by treatment, and applied and watered prior to herbicide treatment installation. Thus, each treatment plot had the same nutrition.

Environmental conditions of the study installation, application being on May 1, 1996, included 69° F. air temperature and 74° F. soil temperature following several days of warm weather. Relative humidity was 50 percent. Soil moisture was 70 percent of field capacity. Winds were easterly at 2–3 MPH under a 60 percent cloud cover.

Duncan's multiple range tests were the primary statistical tool. Nine of these 19 tests were of data composited from each measurement date, a statistic estimating consumer evaluation of weed & feed performance.

TABLE I

FORMULATION OF FIVE TESTED MICRO SIZE WEED & FEED CARRIERS (A–E) TO PRODUCE COMPARABLE COVERAGE (PARTICLE COUNT PER UNIT AREA) COMPARED TO A REGULAR SIZE CONTROL (F).

| | | | | | CARRIER | |
| --- | --- | --- | --- | --- | --- | --- |
| | | REL. BULK | DMB | | LB/A | PARTICLES/FT$^2$ |
| CARRIER | SIZE | DENSITY | % AE | LB AE | (APPROXIMATE) | |
| (A) MICRO SIZE UREA | MICRO | 1.00 | 1.04 | 2.0 | 200 | 3400 |
| (B) MICRO POLY-COAT | MICRO | 0.95 | 0.99 | 2.0 | 200 | 3400 |
| (C) MICRO COMMERCIAL TURF BUILDER & FERTILIZER (CFC)* | MICRO | 0.53 | 1.90 | 2.0 | 105 | 3400 |
| (D) MICRO SULFATE OF POTASH | MICRO | 2.00 | 0.55 | 2.0 | 333 | 3400 |
| (E) MICRO PEANUT HULL GRANULE | MICRO | 0.65 | 1.67 | 2.0 | 118 | 3400 |
| (F) REGULAR SIZE UREA | REGULAR | 1.00 | 1.00 | 2.0 | 200 | 240 |

*THIS CFC PRODUCT WAS SCREENED TO REMOVE ALL LARGE AND VERY SMALL PARTICLES SO THAT ALL PARTICLES OF THE PRODUCT WERE MICRO SIZE.
DMB = THE BRAND ACRONYM FOR THE POST-EMERGENCE HERBICIDES - 2,4-D,MCPP, DICAMBA ( BANVEL).
AE = ACID EQUIVALENT
LB AE = POUNDS OF AE/ACRE
LB/A = POUNDS/ACRE

RESULTS

Results of the study through 28 days after treatment (DAT) were uncomplicated and unambiguous. Micro size carriers were substantially better than the regular size alternative. Micro size urea demonstrated consistent if slight advantage to micro size polymer coated urea, but both were statistically superior to all other carriers (Table 2).

Performance of carriers was ranked by both clover and plantain control at 28 DAT and for the average composited from three measurement dates. Rank of carriers was identical in each instance (Table 2). Much of the remaining broadleaf vegetation in treatments was damaged, and most damaged plants ultimately died.

Micro size ureas provided 77 percent control of clover and plantain at 28 (DAT); regular size urea, least effective among the six tested carriers, provided 48 percent control. Selection of micro size carriers yielded 60 percent improvement in broadleaf control at the same herbicide rate compared to regular size urea carrier.

Peanut hull and sulfate of potash carriers were comparable in performance to each other through 28 DAT; mean control was 64 percent. While providing significantly better weed control than regular size urea, these did not provide control comparative with the micro size ureas.

The commercial turf builder fertilizer carrier (CFC) produced 71 percent control of tested broadleaves. Control of clover by this carrier was equivalent to the micro size ureas, 74 vs 77 percent at 28 DAT. However, this carrier was significantly less effective on plantain than micro size ureas, 67 vs 78 percent control.

Statistically, at 28 DAT, micro size urea and micro size polymer coated urea were indistinguishable, and unambiguously superior to regular size urea. Clover control from micro size sulfate of potash and micro size peanut hull was not comparable to the micro size ureas, nor was plantain control when measurements were composited (Table 2).

Clover control from CFC was not different than that of the micro size ureas at 28 DAT. Plantain control was sufficient to statistically rank CFC with the micro ureas at each measurement date, but not when increased sensitivity was achieved by compositing measurements. Neither did the Duncan's test differentiate CFC from the micro ureas in overall performance (Table 2).

40 DAT Results

At 40 DAT, treatments remained viable. Study wide control improved from 67 to 74 percent during 28–40 DAT. Much of the remaining broadleaf vegetation exhibited herbicide damage.

By 40 DAT micro size peanut hull carrier control of plantain improved dramatically. Plantain control during 28–40 DAT increased 26 percentage points from 63 to 89 percent. Micro size peanut hull carrier was numerically superior to other carriers, and statistically comparable to the micro size ureas. The other durable carriers, CFC and micro size polymer coated urea posted improvement of 11 and 8 points respectively. Plantain control by soluble carrier; improved an average three percentage points during 28–40 DAT.

TABLE 2

PERFORMANCE OF DMB WEED & FEED CARRIER FORMULATIONS DURING 7-28 DAT IN CONTROLLING WHITE CLOVER AND PLANTAIN.

| | RANKED BY 28 DAT PERFORMANCE[1] | | | | | |
|---|---|---|---|---|---|---|
| | CLOVER CONTROL DAYS AFTER TREATMENT | | | PLANTAIN CONTROL DAYS AFTER TREATMENT | | |
| CARRIER | 7 | 15 | 28 | 7 | 15 | 28 |
| MICRO SIZE UREA | 38a | 60a | 78a | 26a | 38a | 80a |
| MICRO POLY-COAT UREA | 30ab | 56a | 76a | 26a | 38a | 75a |
| MICRO CFC | 30ab | 54a | 74a | 20ab | 29a | 67a |
| MICRO SULFATE OF POTASH | 20c | 38b | 64b | 26a | 18b | 66a |
| MICRO PEANUT HULL GRANULE | 22bc | 36b | 64b | 17ab | 29a | 63ab |
| REGULAR SIZE UREA | 10d | 32b | 50c | 14b | 16b | 45b |
| UNTREATED | 0e | 0c | 0d | 0c | 0c | 0c |
| AVERAGE (6 TMT) | 25 | 46 | 66 | 22 | 28 | 67 |

CARRIER RANKED BY 7-28 DAT COMPOSITE PERFORMANCE MEASUREMENTS[1]

| | CLOVER | PLANTAIN | BOTH |
|---|---|---|---|
| MICRO SIZE UREA | 59a | 48a | 53a |
| MICRO POLY-COAT UREA | 54a | 46a | 50a |
| MICRO CFC | 53a | 39b | 46ab |
| MICRO SULFATE OF POTASH | 41b | 37b | 39bc |
| MICRO PEANUT HULL GRANULE | 41b | 36b | 38bc |
| REGULAR SIZE UREA | 31c | 25c | 28c |

[1]PERCENT CONTROL MEANS IDENTIFIED BY THE SAME LETTER ARE STATISTICALLY UNDIFFERENTIATED AT 95 PERCENT CERTAINTY. DUNCAN'S MULTIPLE RANGE TEST, n = 5.

TABLE 3

PERFORMANCE OF DMB WEED & FEED CARRIER FORMULATIONS DURING 7-40 DAT IN CONTROLLING WHITE CLOVER AND PLANTAIN.

| CARRIER | RANKED BY 49 DAT PERFORMANCE[1] | | | |
|---|---|---|---|---|
| | CLOVER | | PLANTAIN | |
| MICRO POLY-COAT | 84a | MICRO PEANUT HULL GRANULE | 89a | |
| MICRO SIZE UREA | 82a | MICRO POLY-COAT UREA | 83ab | |
| MICRO CFC | 80ab | MICRO SIZE UREA | 80ab | |
| MICRO SULFATE OF POTASH | 72bc | MICRO CFC | 78bc | |
| MICRO PEANUT HULL GRANULE | 68c | MICRO SULFATE OF POTASH | 70c | |
| REGULAR SIZE UREA | 56d | REGULAR SIZE UREA | 50d | |
| AVERAGE | 74 | | 75 | |

TABLE 3-continued

PERFORMANCE OF DMB WEED & FEED CARRIER FORMULATIONS DURING
7-40 DAT IN CONTROLLING WHITE CLOVER AND PLANTAIN.

CARRIER RANKED BY 7-40 DAT COMPOSITE PERFORMANCE MEASUREMENTS[1]

|  | CLOVER | PLANTAIN | BOTH |
| --- | --- | --- | --- |
| MICRO SIZE UREA | 63a | 56a | 59a |
| MICRO POLY-COAT UREA | 62a | 56a | 59a |
| MICRO CFC | 60a | 49ab | 54ab |
| MICRO PEANUT HULL GRANULE | 48b | 50ab | 49b |
| MICRO SULFATE OF POTASH | 49b | 45b | 47b |
| REGULAR SIZE UREA | 37c | 31c | 34c |

[1]PERCENT CONTROL MEANS IDENTIFIED BY THE SAME LETTER ARE STATISTICALLY UNDIFFERENTIATED AT 95 PERCENT CERTAINTY. DUNCAN'S MULTIPLE RANGE TEST, n = 5.

Micro size polymer coated urea, marginally inferior in weed control to micro size urea in plantain control at 28 DAT, increased control by 8 percentage points to edge ahead by 40 DAT as plantain control but micro size urea did not improve. Plantain control in sulfate of potash and regular urea carrier treatments improved slightly, 4–5 percentage points, during 28–40 DAT.

Clover control by each carrier improved 4–8 percentage points during 28–40 DAT without apparent pattern. Ranking of treatments by clover control remained unaltered throughout 7–40 DAT, the micro size ureas and CFC providing superior control. Species characteristics clearly influence potential herbicide transfer. Clover does not, for example, possess plantain's acutely angled leaf axle which can trap and retain applied carrier.

Composited performance of the two micro size ureas at 40 DAT was identical at 59 percent, numerically superior to all other carriers, and statistically equaled only by CFC. The strong performance of micro size peanut hull granule carrier on plantain during 28–40 DAT resulted in ranking it among superior composite plantain control carriers, slightly better than CFC but numerically inferior to the micro size ureas. Superior composite performance of the micro size ureas on clover across 7–40 DAT was statistically equaled by CFC.

TABLE 4

PERFORMANCE OF DMB WEED & FEED CARRIER FORMULATIONS DURING
7-56 DAT IN CONTROLLING WHITE CLOVER AND PLANTAIN.

CARRIER RANKED BY 56 DAT PERFORMANCE[1]

| CLOVER | | PLANTAIN | |
| --- | --- | --- | --- |
| MICRO POLY-COAT | 82a | MICRO CFC | 91a |
| MICRO SIZE UREA | 80a | MICRO POLY-COAT UREA | 90a |
| MICRO PEANUT HULL GRANULE | 74ab | MICRO PEANUT HULL GRANULE | 89a |
| MICRO CFC | 70b | MICRO SIZE UREA | 85a |
| MICRO SULFATE OF POTASH | 68b | MICRO SULFATE OF POTASH | 84a |
| REGULAR SIZE UREA | 46c | REGULAR SIZE UREA | 53c |
| AVERAGE | 70 |  | 82 |

CARRIER RANKED BY 7-56 DAT COMPOSITE PERFORMANCE MEASUREMENTS[1]

|  | CLOVER | PLANTAIN | BOTH |
| --- | --- | --- | --- |
| MICRO SIZE UREA | 66a | 63a | 64a |
| MICRO POLY-COAT UREA | 66a | 62a | 64a |
| MICRO CFC | 62ab | 57ab | 59ab |
| MICRO PEANUT HULL GRANULE | 53b | 58ab | 56b |
| MICRO SULFATE OF POTASH | 53b | 53b | 53b |
| REGULAR SIZE UREA | 39c | 35c | 37c |

[1]PERCENT CONTROL MEANS IDENTIFIED BY THE SAME LETTER ARE STATISTICALLY UNDIFFERENTIATED AT 95 PERCENT CERTAINTY. DUNCAN'S MULTIPLE RANGE TEST, n = 5.

56 DAT Results (Table 4)

Vegetative recovery was evident by 56 DAT, signaling an end to intensive study. Clover populations were recovering in certain treatments. Control diminished from 74 to 70 percent during 40–56 DAT (Table 3). While plantain control improved from 75 to 82 percent, remaining plantain was maturing into reproductive state.

Prolonged decline of damaged plantain observed during 28–40 DAT continued during 40–56 DAT, most conspicuously in CFC and micro size sulfate of potash carrier treatments where substantial populations of plantain remained after 40 DAT. Control in these treatments improved from 78 to 91 and 70 to 84 percent respectively. By 56 DAT these treatments were similar in appearance and statistically identical to those of the micro size ureas and peanut hull granule carrier treatments. Regular size urea was the lone inferior carrier treatment of plantain at 56 DAT.

Micro size peanut hull granule carrier was the only treatment which demonstrated continued significant clover control during 40–56 DAT (Table 4). Control improved 68 to 74 percent, ranking micro size peanut hull with the micro size ureas as a superior treatment.

During 40–56 DAT clover populations changed little in micro size urea treatments which, at 80–82 percent control, remained the best clover control treatments, numerically superior to micro size peanut hull granule (74 percent).

Clover density increased 4 percentage points in micro size sulfate of potash treatments. Clover recovery was most evident in CFC and regular size urea treatments where clover density increased by 10 percentage points during 40–56 DAT.

At 56 DAT clover control by micro size peanut hull granules, CFC and micro size sulfate of potash carrier were statistically equivalent (68–74 percent) intermediate treatments. Regular size urea delivered an inferior 46 percent control, similar to 40 DAT performance.

Final composited performance of both broadleaf species at all measurement dates by the two micro size ureas remained identical and statistically superior to all other treatments except CFC, a pattern that persisted throughout the study. Other than the superior micro size ureas and the regular size urea, which provided significantly inferior control, the other tested carriers delivered statistically intermediate performances.

Micro size ureas were statistically superior to carriers other than CFC in composite clover control and to micro size peanut hull granule and CFC in composite plantain control. CFC, micro size peanut hull granule, and micro size sulfate of potash were statistically undifferentiated and of intermediate effectiveness in both clover and plantain control. Regular size urea was an inferior weed & feed carrier.

Braodleaf Control Characteritc of Carriers Micro Size Ureas

Micro size urea prill and micro size polymer coated urea prill were statistically among superior treatments at each measurement and displayed composited numerical superiority to all other treatments throughout the study. Differences between micro size urea and micro size polymer coated urea carriers are best discussed by considering these together as their performance was very similar.

Micro size ureas as weed & feed carriers demonstrated rapid efficient transfer of DMB, establishing control of clover and plantain superior to most carriers by 7 DAT and expanding this advantage over other carriers through 15 and 28 DAT when control reached 80 percent.

Micro size urea marginally out performed micro size polymer coated urea during 7–28 DAT, perhaps reflecting superior early herbicide delivery by the uncoated, hence more soluble, micro size urea carrier. During 28–56 DAT micro size polymer coated urea out performed micro size urea (Tables 3 & 4), perhaps reflecting superior persistent herbicide delivery by this more lasting carrier. Initial control by micro size polymer coated urea was competitive with micro size urea so that micro size polymer coated urea met or slightly exceeded, through increased residual control, the composite control standard established by micro size urea at 28 DAT.

Micro size urea delivered little additional control after 28 DAT, but by 28 DAT few damaged plants remained to recover. While performance of micro size urea was equaled or marginally bettered by treatments offering residual continued control during 40–56 DAT, its rapid performance and excellent control foreclosed any possibility that treatments offering significantly weaker initial control could become competitive in composited evaluation through superior residual effectiveness.

Micro Size CFC

The CFC was usually third to the micro size ureas and among statistically superior carriers throughout the study. This carrier exhibited good initial control characteristics and continued residual performance on plantain through 56 DAT. At 56 DAT CFC was the numerically superior plantain treatment. CFC was among superior clover control carriers through 40 DAT. During 40–56 DAT clover populations increased 10 percent in CFC treatment, dropping CFC into a second tier of treatments. CFC ranked consistently third behind the micro size ureas in composited control, a statistic estimating consumer evaluation. A highly successful commercial carrier, CFC is an excellent standard of comparison for the various fertilizer materials used in fertilizer blends as carriers.

Micro Size Peanut Hull Granule

Micro size peanut hull granule offers attractive theoretical advantages as a carrier. A very low density, fibrous, angular product, it should cling well to contacted vegetation and offer superior opportunity to transfer herbicide. However, micro size peanut hull granule is adsorbent, and extraction of herbicide from peanut hull proved difficult when tested. Contact advantages of micro size peanut hull granules were presumably offset by slow herbicide transfer from carrier to vegetation, yielding inferior 7–28 DAT performance.

Perhaps incremental DMB delivery across time by the persistent non-soluble micro size peanut hull granule carrier, after delivery by soluble carriers dissipated, explains break away performance on plantain during 28–40 DAT (Table 3). Additionally, micro size peanut hull granule was the only carrier which exhibited significant additional clover control during 40–56 DAT when clover populations were elsewhere recovering (Table 4).

Micro size peanut hull granule was among statistically superior plantain control treatments throughout the study, although numerically far beneath micro treatments during 7–28 DAT. A premier plantain control carrier after 40 DAT (89 percent control), micro size peanut hull granule carrier also statistically joined the best clover control carriers (74 percent control) at 56 DAT (Table 4). Inferior initial control from micro size peanut hull granule carrier, a characteristic presumably disfavored by consumers, rendered the carrier non-competitive in composited ratings.

Micro Size Sulfate of Potash Granule

Micro size sulfate of potash was a carrier of intermediate performance at 7 DAT and retained intermediate ranking in clover and plantain control throughout the study. During 7–28 DAT micro size sulfate of potash tracked micro size peanut hull granule in performance, but exhibited limited residual control of plantain during 28–56 DAT, and of clover until 40 DAT.

Regular Size Urea Granule

Regular size urea granule exhibited initial control inferior to other carriers, presumably as a result of coverage, particle distribution per unit area and its higher particle weight. Regular size urea exhibited limited residual control and fell further behind competing carriers as the study advanced. Regular size urea granule was significantly inferior to other tested carriers at each measurement in the study.

Regular size urea granule was applied at 240 particles/sq.ft. compared to 3400 particles/sq.ft. of other carriers, and particles were significantly larger and heavier than those of other carriers. Each of these characteristics adversely affected effective contact and retention to weed foliage by regular size urea.

While there is some variability in the results of this study, which usually is experienced in herbicide testing, there is clear evidence from these tests that the micro size urea prill is the best of the four micro-sized components evaluated, including the lightweight micro size peanut hull particle. Further, the micro size urea prill and micro size polymer-coated urea prill are at least equal to, if not superior to, the screened micro size CFC, a homogeneous NPK particle. Most importantly, all micro-sized particle treatments were greatly superior in weed control performance to the regular-sized urea particles.

In addition to field research set forth hereinbefore, a comparison of effectiveness of spray applied liquid herbicides with granular weed & feed products has been carried out. Thus, comparison of liquid droplet particles and W&F granule or prill particles are given below:

TABLE 5

| HERBICIDE PRODUCTS | PARTICLE TYPE | PARTICLE SIZE - MICRONS | |
|---|---|---|---|
| | | RANGE | NOMINAL |
| LIQUID NON-DRIFT SPRAY | LIQUID DROPLETS | 500–2000 | 1500 |
| GRANULAR W&F | | | |
| A. REGULAR SIZE | SOLID GRANULES | 1500–3000 | 2500 |
| B. MICRO SIZE | SOLID GRANULES OR PRILLS | 500–1500 | 1000 |

A study of the effectiveness of the application of the herbicide products set forth in Table 5 clearly establishes that the micro-sized granular weed & feed products are greatly superior to the regular-sized weed & feed products and approach the effectiveness of liquid spray application of herbicides. The micro-sized weed & feed products, however, do not require the additional step of applying fertilizer and, further, do not have the potential for the detrimental over-spray and spray drift associated with liquid applications. Accordingly, the micro size products of the present invention have clear unexpected superiority over the conventional regular-size weed & feed products.

EXAMPLES OF PRESENTLY PREFERRED EMBODIMENTS

Example 1

Micro size fertilizer particles of urea, 40% of total, mono-ammonium phosphate, 20% of total, and potassium phosphate, 40% of total, were blended together to provide a uniform fertilizer blend. These particles were then impregnated with 2% by weight DMB based on the total weight of the blend. All of the micro size fertilizer particles had a particle size within the range of 500 to 1500 microns. This product provided excellent broadleaf control.

Example 2

Micro size urea prill particles having a particle size within the range of 500 to 1500 microns are coated with a 0.5% by weight DMB based on the weight of the urea. This product provided excellent weed control.

Example 3

Example 2 above was repeated except that the micro size urea prill, 60% by weight of the total, was blended with micro size peanut hull particles, 40% by weight of the total, the prill urea and peanut hull particles having a particle size within the range 500 to 1500 microns. The blend was impregnated with 6% by weight DMB based on the total weight of the blend. This weed & feed product provided excellent weed control over a period of 56 days after treatment which was significantly superior to identically formulated and applied regular size, 1500–3000 microns, weed & feed.

As will be apparent to one skilled in the art, various modifications can be made within the scope of the aforesaid description. Such modifications being within the ability of one skilled in the art form a part of the present invention and are embraced by the appended claims.

What is claimed is:

1. A composition for killing emerged broad leaf weeds comprising a particulate fertilizer blend including urea particles, ammonium phosphate particles and potassium phosphate particles, all of said particles having a particle size within the range of 500 to 1500 microns and being coated with a systemic auxinic herbicide in an amount effective to kill broad leaf weeds when said composition is applied to broad leaf weed foliage.

2. The composition of claim 1 wherein said fertilized particles are polymer coated.

3. A composition for killing emerged broad leaf weeds comprising a particulate fertilizer blend including urea particles, and particles which are a source of ammonium, phosphorous and potassium, hall of said particles having a particle size within the range of 500 to 1500 microns and being coated with a systemic auxinic herbicide in an amount. effective to kill broad leaf weeds when said composition is; applied to broad leaf weed foliage.

4. The composition of claim 3 wherein the source of ammonium is mono-ammonium phosphate.

5. The composition of claim 3 wherein said source of potassium is potassium phosphate.

6. The composition of claim 3 wherein said composition further includes a low density inert filler material having a particle size within the range of 500 to 1500 microns.

7. The composition of claim 6 wherein said inert filler material is selected from the group consisting of corn cob granules, peanut granules and clay granules.

8. Method of killing emerged broad leaf weeds comprising 1) providing a weed and feed composition comprising a blend of particulate fertilizers, said particulate fertilizers having a particle size within the range of 500 to 1500 microns and being coated with a systemic auxinic herbicide in an amount effective to kill emerged broad leaf weeds and 2) applying said fertilizer composition to turf containing broad leaf weeds, whereby said broad leaf weeds are killed.

* * * * *

UNITED STATES PATENT AND TRADEMARK OFFICE
CERTIFICATE OF CORRECTION

PATENT NO. : 6,180,565 B1
DATED : January 30, 2001
INVENTOR(S) : John H. Detrick It is certified that error appears in the above-identified patent and that said Letters Patent is hereby corrected as shown below:

Column 11,
Line 34, the heading and subheading "Braodleaf Control Characteritc of Carriers Micro Size Ureas" should read -- Broadleaf Control Characteristics of Carriers Micro size ureas --.

Column 14, claim 3,
Line 34, "hall" should read -- all --.

Signed and Sealed this

Thirteenth Day of November, 2001

Attest:

NICHOLAS P. GODICI
Attesting Officer
Acting Director of the United States Patent and Trademark Office